(12) United States Patent
Mukundan et al.

(10) Patent No.: US 7,575,709 B2
(45) Date of Patent: Aug. 18, 2009

(54) TAPE-CAST SENSORS AND METHOD OF MAKING

(75) Inventors: Rangachary Mukundan, Santa Fe, NM (US); Eric L. Brosha, Los Alamos, NM (US); Fernando H. Garzon, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 1031 days.

(21) Appl. No.: 11/110,086

(22) Filed: Apr. 19, 2005

(65) Prior Publication Data

US 2006/0231987 A1    Oct. 19, 2006

(51) Int. Cl.
     C03B 29/00     (2006.01)
     C04B 35/64     (2006.01)
     G01N 27/26     (2006.01)
     B32B 15/00     (2006.01)
     B32B 19/00     (2006.01)

(52) U.S. Cl. .......... 264/618; 156/89.12; 156/89.14; 204/421; 204/424; 204/426; 428/209; 428/701

(58) Field of Classification Search .......... 156/89.12; 204/421; 264/618
See application file for complete search history.

(56) References Cited

U.S. PATENT DOCUMENTS

| | | | |
|---|---|---|---|
| 3,192,086 A | 6/1965 | Gyurk et al. | |
| 4,766,027 A | 8/1988 | Burn | |
| 4,852,227 A | 8/1989 | Burks | |
| 4,957,673 A * | 9/1990 | Schroeder et al. | 264/643 |
| 6,051,123 A | 4/2000 | Joshi et al. | |
| 6,551,497 B1 | 4/2003 | Gao et al. | |
| 6,605,202 B1 | 8/2003 | Mukundan et al. | |
| 6,656,336 B2 | 12/2003 | Mukundan et al. | |
| 6,743,534 B2 * | 6/2004 | Lautzenhiser et al. | 428/701 |
| 6,800,158 B2 | 10/2004 | Polikarpus et al. | |

OTHER PUBLICATIONS

Miura, Norio et al., Mixed-potential-type propylene sensor based on stabilized zirconia and oxide electrode, Electrochemistry, 2, (2000), 77-80.*
Miura et al., "Mixed-Potential-Type Propylene Sensor Based on Stabilized Zirconia and Oxide Electrode," Electrochemistry Communications 2 (2000) 77-80.
Mukundan et al., "Ceria-Electrolyte-Based Mixed Potential Sensors for the Detection of Hydrocarbons and Carbon Monoxide," Electrochemical and Solid-State Letters, 2 (8) 412-141 (1999).
Miura et al., "High-Temperature Potentiometric/Amperometric $NO_x$ Sensors combining stabilized Zirconia with Mixed-metal Oxide Electrode," Sensors and Actuators B 52 (1998) 169-178.

* cited by examiner

*Primary Examiner*—Philip C Tucker
*Assistant Examiner*—Alex Efta
(74) *Attorney, Agent, or Firm*—Robert P. Santandrea; Juliet A. Jones (57) ABSTRACT

A method of making electrochemical sensors in which an electrolyte material is cast into a tape. Prefabricated electrodes are then partially embedded between two wet layers of the electrolyte tape to form a green sensor, and the green sensor is then heated to sinter the electrolyte tape around the electrodes. The resulting sensors can be used in applications such as, but not limited to, combustion control, environmental monitoring, and explosive detection. A electrochemical sensor formed by the tape-casting method is also disclosed.

18 Claims, 8 Drawing Sheets

TAPE-CAST SENSORS AND METHOD OF MAKING

STATEMENT REGARDING FEDERAL RIGHTS

This invention was made with government support under Contract No. W-7405-ENG-36, awarded by the U.S. Department of Energy. The government has certain rights in the invention.

BACKGROUND OF INVENTION

The invention relates to gas sensors. More particularly, the invention relates to a method of making mixed potential gas sensors. Even more particularly, the invention relates to an electrochemical sensor formed from a tape-cast electrolyte and a plurality of electrodes.

Electrochemical gas sensors have been developed for combustion control and environmental monitoring applications. These devices typically comprise two different catalytic electrodes deposited on a solid electrolyte. Multiple oxidation-reduction (redox) reactions occur between gaseous species and the electrodes, causing mixed potentials of differing magnitude to occur between the dissimilar electrodes. Sensors comprising metal and metal-oxide electrodes have been used to detect species such as carbon monoxide (CO), nitrogen oxides, such as NO and $NO_2$, (also referred to hereinafter as "NOx"), and hydrocarbons. Although these sensors are responsive to reducing gases, their lack of stability, reproducibility, and selectivity has hindered further development and widespread use.

Mixed potential sensors have been made by embedding and sintering electrodes, such as metal wires and oxide pellets, in an electrolyte. This process requires that individual sensors be pressed by hand, and thus does not lend itself to the large-scale manufacture of sensors. Thin film manufacturing techniques have been used as well to make sensors. Although thin film techniques are easily adaptable to large-scale production, they require the use of expensive vacuum systems. Moreover, the use of thin film techniques is currently limited to the manufacture of hydrocarbon sensors.

Current methods of making mixed potential sensors are not readily adaptable to large-scale production. In addition, the sensors produced by these methods lack the stability, reproducibility, and selectivity that are needed to make them suitable for widespread use. Therefore, what is needed is a simplified method of making mixed potential sensors. What is also needed is a method of making sensors having improved thermal stability, reproducibility, and selectivity.

SUMMARY OF INVENTION

The present invention meets these and other needs by providing a method of making mixed potential sensors in which electrolyte material is cast into a tape. Prefabricated electrodes are then partially embedded between two wet layers of the tape to form a green sensor, and the green sensor is then heated to sinter the electrolyte around the electrodes. The resulting sensors can be used in applications such as, but not limited to, combustion control, environmental monitoring, and explosive detection.

Accordingly, one aspect of the invention is to provide a method of making a solid state electrochemical sensor. The sensor comprises a plurality of electrodes partially disposed within an electrolyte. The method comprises the steps of: providing the electrolyte; casting the electrolyte to form an electrolyte tape, wherein the electrolyte tape has a wet first surface; providing the plurality of electrodes; contacting a portion of each of the plurality of electrodes with a first portion of the wet first surface; contacting a second portion of the wet first surface with the portion of each of the plurality of electrodes and the first portion of the wet first surface, wherein each of the plurality of electrodes is partially embedded within the electrolyte; drying the electrolyte tape and the partially enclosed first and second electrodes to form a green sensor body; and sintering the green sensor body to form the solid state electrochemical sensor.

A second aspect of the invention is to provide a method of making a green sensor body. The method comprises the steps of: providing an electrolyte; casting the electrolyte to form an electrolyte tape, wherein the electrolyte tape has a wet first surface in contact with a carrier and a second surface opposite the wet first surface, the second surface being exposed to air; partially drying the second surface for a predetermined time; reversing the electrolyte tape such that the wet first surface is exposed to air and the partially dried second surface contacts the carrier; providing at least a first electrode and a second electrode; contacting a portion of each of the first electrode and the second electrode with a first portion of the wet first surface; contacting a second portion of the wet first surface with the portion of the first electrode and the second electrode and the first portion of the first surface, wherein the first and second electrodes are partially embedded within the electrolyte tape; and drying the electrolyte tape and the partially enclosed first and second electrodes to form a green sensor body.

A third aspect of the invention is to provide a method of making an electrochemical sensor. The sensor comprises at least a first electrode and a second electrode partially disposed within an electrolyte. The method comprises the steps of: providing the electrolyte; casting the electrolyte into an electrolyte tape, wherein the electrolyte tape has a wet first surface in contact with a carrier and a second surface opposite the first surface, the second surface being exposed to air; partially drying the second surface for a predetermined time; reversing the electrolyte tape such that the wet first surface is exposed to air and the partially dried second surface contacts the carrier; providing at least a first electrode and a second electrode; contacting a portion of the first electrode and a portion of the second electrode with a first portion of the wet first surface; contacting a second portion of the wet first surface with the portion of the first electrode and the portion of the second electrode and the first portion of the wet first surface, wherein the first and second electrodes are partially embedded within the electrolyte tape; drying the electrolyte tape and the partially enclosed first and second electrodes to form a green sensor body; and sintering the green sensor body to form the solid state mixed potential sensor.

A fourth aspect of the invention is to provide an electrochemical sensor. The sensor comprises: a tape-cast electrolyte, the tape-cast electrolyte having a first portion and a second portion; and a plurality of electrodes, wherein a portion of each of the plurality of electrodes is embedded between the first portion and the second portion of the tape-cast electrolyte.

A fifth aspect of the invention is to provide a solid state electrochemical sensor. The sensor comprises a plurality of electrodes partially disposed within an electrolyte. The sensor is formed by: casting the electrolyte into an electrolyte tape, wherein the electrolyte tape has a wet first surface; contacting a portion of each of the plurality of electrodes with a first portion of the wet first surface; contacting a second portion of the wet first surface with the portion of each of the plurality of electrodes and the first portion of the wet first surface, wherein each of the plurality of electrodes is partially embedded within the electrolyte tape; drying the electrolyte tape and the partially embedded first and second electrodes to form a green sensor body; and sintering the green sensor body to form the solid state mixed potential sensor.

These and other aspects, advantages, and salient features of the present invention will become apparent from the following detailed description, the accompanying drawings, and the appended claims.

DETAILED DESCRIPTION

In the following description, like reference characters designate like or corresponding parts throughout the several views shown in the figures. It is also understood that terms such as "top," "bottom," "outward," "inward," and the like are words of convenience and are not to be construed as limiting terms. In addition, whenever a group is described as either comprising or consisting of at least one of a group of elements and combinations thereof, it is understood that the group may comprise or consist of any number of those elements recited, either individually or in combination with each other.

Figure 1:
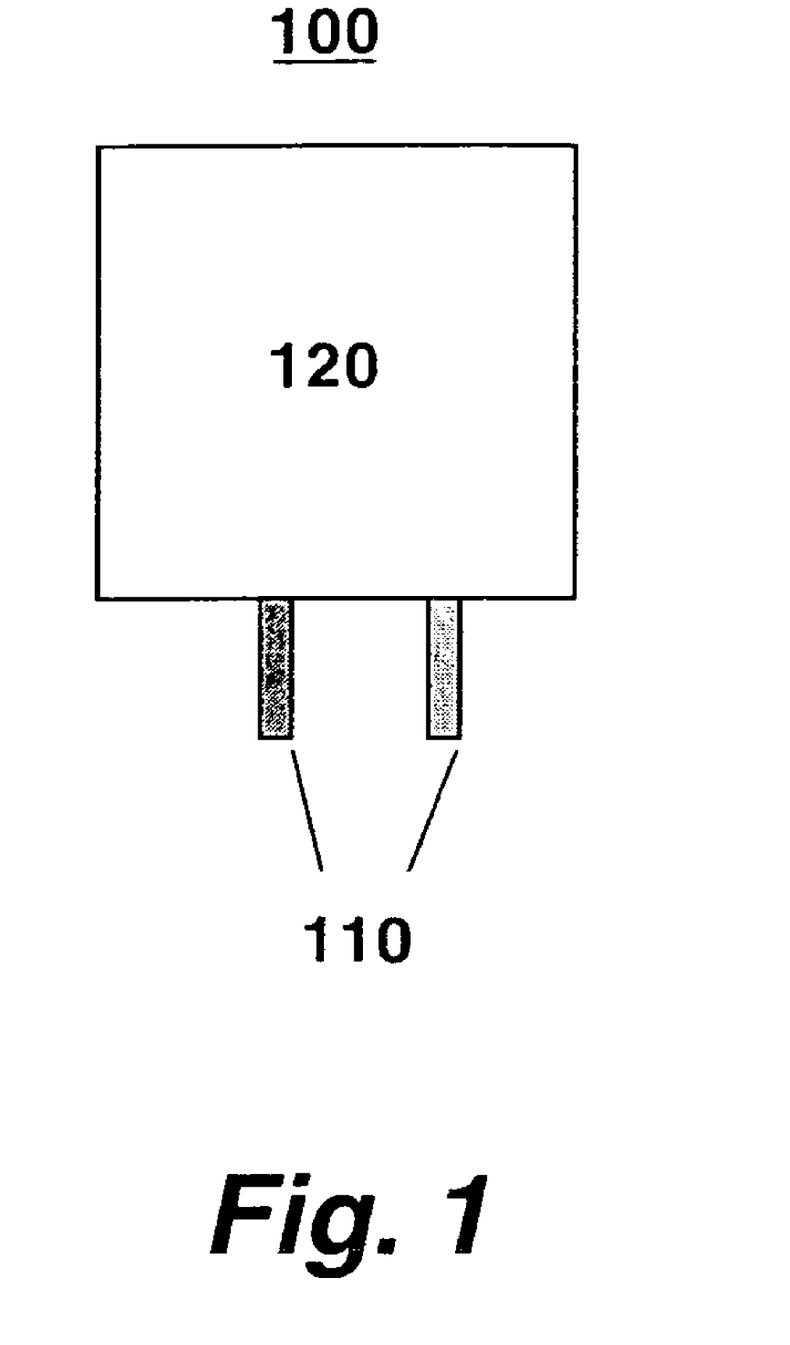
FIG. 1 is a schematic representation of an electrochemical sensor of the present invention.

Referring to the drawings in general and to FIG. 1 in particular, it will be understood that the illustrations are for the purpose of describing a particular embodiment of the invention and are not intended to limit the invention thereto.

Turning to FIG. 1, a schematic representation of an electrochemical sensor of the present invention is shown. Electrochemical sensor (referred to hereinafter as "sensor") 100 comprises a plurality of electrodes 110. A portion of each of the plurality of electrodes 110 is embedded between two portions of a tape-cast electrolyte 120. In most instances, the sensor has two electrodes. However, where detection of multiple gaseous species by sensor 100 is desired, sensor 100 may have more than two electrodes 110. The plurality of electrodes 110 includes at least two electrodes that are dissimilar to each other. When a gaseous specie (or species) catalytically reacts with each of the dissimilar electrodes, a potential difference is generated between electrodes 110. The potential difference translates into an output signal for electrochemical sensor 100 that corresponds to the concentration of the gaseous specie or species.

In one embodiment, electrochemical sensor 100 is a non-Nernstian sensor. For the purposes of understanding the invention, a non-Nernstian sensor is an electrochemical sensor in which the voltage deviates from the theoretical voltage obtained when all the gaseous species and charge carriers are in thermodynamic equilibrium with each other. In a particular embodiment, the non-Nernstian sensor is a mixed potential sensor; that is, a non-Nernstian sensor in which the voltage is determined by the reaction rates of at least two species undergoing electrochemical oxidation/reduction reactions at the three-phase electrode/electrolyte/gas interface.

Each of the plurality of electrodes 110 comprises at least one electronically conductive material. The electronically conductive material comprises at least one of an oxide, a metal, a semiconductor, and combinations thereof. The at least one electronically conducting material has an electronic conductivity of greater than 10 mS/cm at a temperature in a range from about 300° C. to about 1000° C. In one embodiment, the electronically conductive material comprises at least one of platinum, gold, a lanthanide-based oxide, a zirconium-based oxide, and combinations thereof. The lanthanide-based oxide is one of: a lanthanum-chromium based oxide, including lanthanum chromium based oxides in which at least one of calcium, strontium, and magnesium has been substituted for a portion of the lanthanum; a lanthanum-cobalt based oxide; a lanthanum-manganese based oxide; combinations thereof, and the like. In one embodiment, the zirconium-based oxide is a terbium-doped zirconium-based oxide. Each of the plurality of electrodes 110 comprises at least one of a metal wire, metal foil, a pellet, a tape, and combinations thereof.

Tape-cast electrolyte 120 comprises an ionic conducting material. In one embodiment, the ionic conducting material is an inorganic oxide that has one of a fluorite crystal structure, a perovskite crystal structure, a brown-millerite crystal structure, a pyrochlore crystal structure, and a beta-alumina crystal structure. Ionic conducting materials used in tape-cast electrolyte 120 include, but are not limited to, yttria stabilized zirconia, gadolinia stabilized ceria, and combinations thereof.

Figure 2:
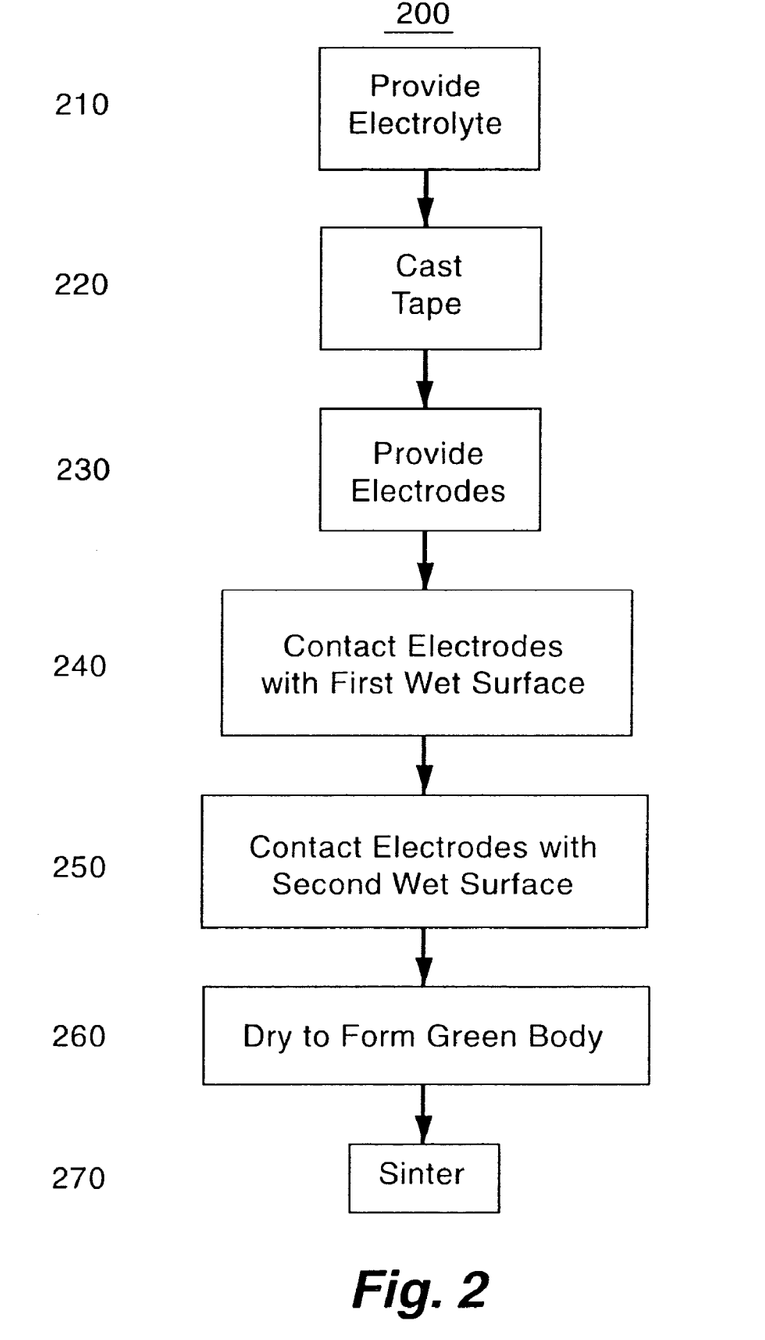
FIG. 2 is a flow chart of a method of a making sensor.

FIG. 2 is a flow chart that illustrates the method 200 of making sensor 100. First, at least one electrolyte, such as, but not limited to, yttria stabilized zirconia or gadolinia stabilized ceria, is provided in powder form (Step 210). The electrolyte powder may be dried. Typically, the powder is dried at a temperature in a range from about 100° C. to about 150° C. for approximately one hour. The dried powder is then mixed with at least one solvent, such as xylene, ethyl alcohol, fish oil, or the like, and ball milled. Plasticizers and binders, such as, but not limited to, S-160, (benzyl butyl phthalate), UCON (polyalkylene glycol), B-98 (polyvinyl butyral), and the like are then added to the mixture of powder and solvent, followed by further ball milling to form a slurry. Ball milling times are generally about 24 hours, and, after milling, the mill is discharged and de-aired for approximately 10 minutes at approximately 20-25 inches (510-635 mm) of Hg.

In Step 220, the slurry is cast as a tape onto a carrier using tape-casting methods that are well known in the art. In one embodiment, the slurry is tape-cast onto a Si-coated Mylar (G10JRM) carrier film using a standard doctor blade apparatus, the apparatus having a gap in a range from about 0.05 inch (about 1.27 mm) to 0.2 inch (about 5.1 mm).

Figure 3A:
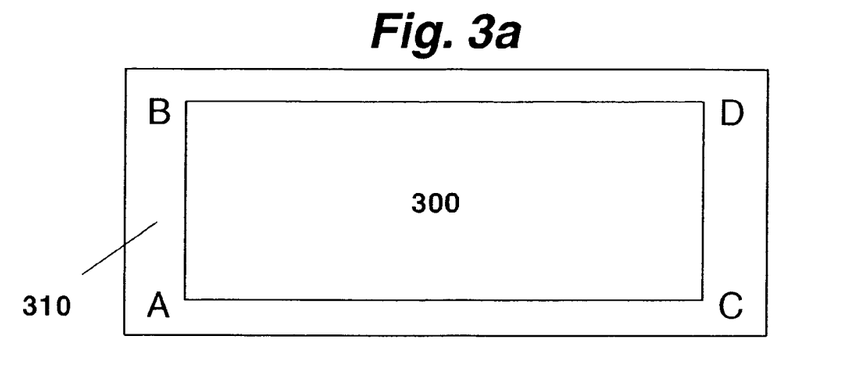
FIG. 3a is a schematic representation of an electrolyte tape-cast onto a carrier.

Once cast, tape 300 is allowed to partially dry. Drying typically takes between approximately 10 to 20 minutes. At this point, the outer face of the tape (i.e., the surface of the tape facing air) is dry and the inner face of the tape in contact with the carrier film is still very wet. The wet inner face of the tape is still sticky or tacky, and is capable of wetting the surface of any material that comes in contact with it. In contrast to the inner face, the dry outer face is not sticky and provides the tape with enough mechanical stability to allow the tape to be handled. The tape is then reversed so as to expose the wet inner face to air while contacting the dry side with the carrier film. FIG. 3a is a schematic diagram showing the tape 300 disposed on carrier 310, with the wet inner face (or surface) of tape 300 facing upward. Characters A, B, C, and D identify the four corners of tape 300.

Figure 3B:
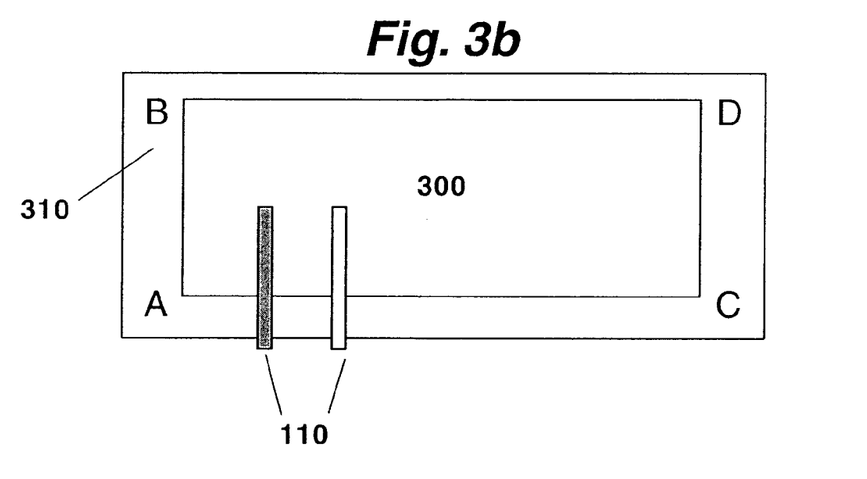
FIG. 3b is a schematic representation showing electrodes in contact with a wet face of a first portion of cast electrolyte tape.
Figure 3C:
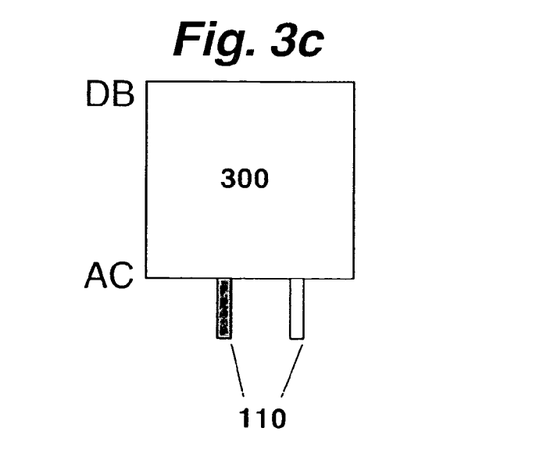
FIG. 3c is a schematic representation showing the cast electrolyte tape folded over to partially enclose the electrodes.

In Step 230, a plurality of electrodes 110, described hereinabove, is provided. Electrodes 110 are pre-fabricated. Electrodes 110 are then brought into contact with the wet inner face (or surface) of a first portion of tape 300 in Step 240. Electrodes 110 may be lightly pressed into the wet inner face FIG. 3b shows electrodes 110 in contact with the wet inner face (or surface) of the first portion of tape 300. In Step 250, a second portion the wet inner face (or surface) of tape 300 is then brought into contact with the plurality of electrodes 110 so as to partially enclose the plurality of electrodes 110 within the tape 300 cast from electrolyte 120. In one embodiment, shown in FIG. 3c, tape 300 is folded on to itself, so that corners C and D of tape 300 meet corners A and B, respectively. As an alternative to folding tape 300 onto itself, another segment of tape 300 having a wet face and a dry face may be placed over the first segment of tape 300, which is already in contact with electrodes 110, so that the wet faces of the different tape segments contact each other such that electrodes 110 are sandwiched or embedded between the wet tapes and are partially covered; i.e., a portion of each electrode 110 extends beyond tape 300 and is exposed. The resulting cast electrolyte tape 300 with partially enclosed electrodes 110 is then allowed to air dry fully to form a green sensor body (Step 260). The green sensor body is then sintered to form sensor 100 in Step 270. In one embodiment, Step 270 includes removal of the binder prior to sintering. In one non-limiting example, the binder is first removed by heating the green sensor body from room temperature to about 500° C. at a rate of about 2° C./min and held at about 500° C. for approximately 1 hour. The green sensor body is then heated from 500° C. to about 625° C. at a rate of about 1° C./min and held at that temperature for about 1 hour. After removal of the binder, the green sensor body is sintered by heating the sensor body to a temperature in the range from about 1000° C. to about 1200° C. at a rate of about 5° C./min. The sensor body held at temperature for about 10 hours, and then allowed to cool to room temperature at a rate of about 5'/min. The sintering temperature is selected to yield a porous electrolyte and also depends upon the particular materials used to form the plurality of electrodes 110 and tape-cast electrolyte 120. For example, gold-based electrodes are sintered at about 1000° C., whereas lanthanum chromite electrodes are sintered at about 1200° C.

Figure 4A:
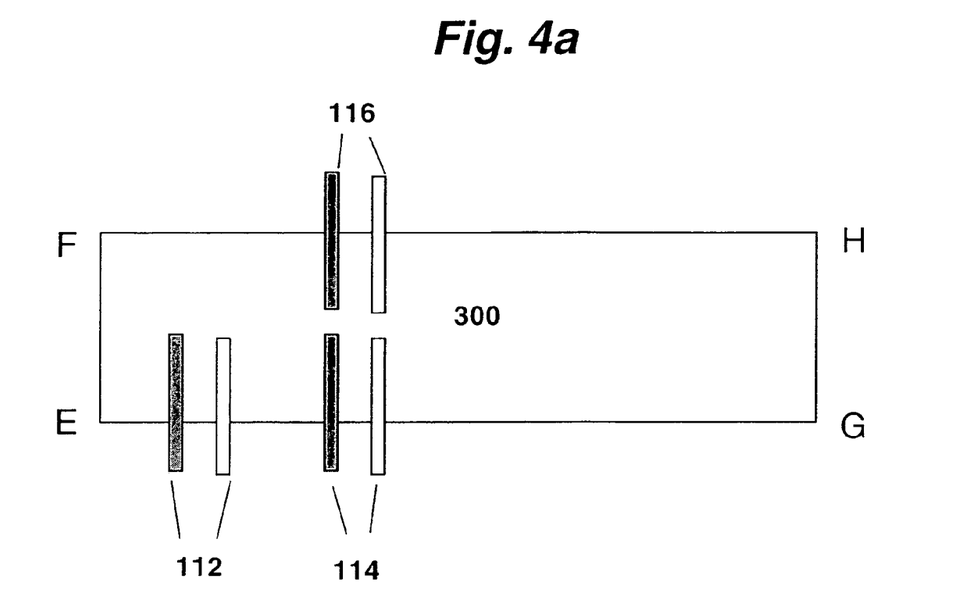
FIG. 4a is a schematic representation showing multiple electrode pairs in contact with a wet face of a first portion of cast electrolyte tape.
Figure 4B:
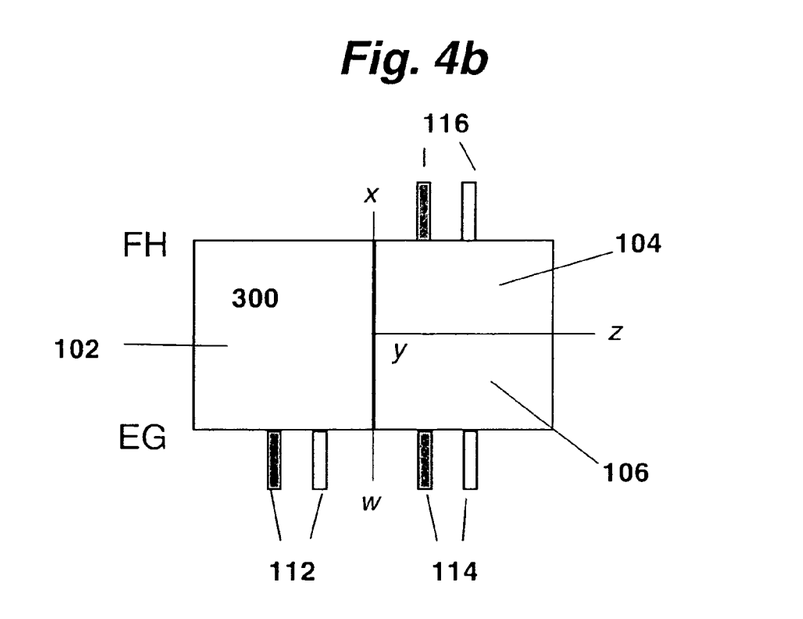
FIG. 4b is a schematic representation showing the cast electrolyte tape folded over to partially enclose the multiple pairs of electrodes.

In another embodiment, method 200 is adapted to prepare a plurality of sensors 100. As shown in FIG. 4a, a number of electrodes 110 sufficient to make a number of 100 sensors may be provided to the wet face or surface of the first potion of tape 300. In the example shown in FIG. 4a, three pairs of dissimilar electrodes 112, 114, 116 are brought into contact with tape 300. A wet face or surface of a second portion of tape 300 is then brought into contact with the electrode pairs and the wet face of the first portion of tape 300 so as to partially enclose the plurality of electrodes 110 within the tape 300 cast from electrolyte 120. In the embodiment shown in FIG. 4b, tape 300 is folded on to itself, so that corners G and H of tape 300 meet corners E and F, respectively. Individual sensors 102, 104, 106 are then be obtained by cutting the green tape 300 along lines wx and yz. The green tape may be cut either by hand, such as by a razor blade or scissors, or by mechanical cutting instruments known in the art. As many electrode combinations as needed may be placed in between the tapes to form multiple sensors. As previously described, the plurality of electrodes 110 may comprise metal wires, metal foils, ceramic pellets, ceramic tapes, and combinations thereof. Whereas the sensors shown FIGS. 1, 3b, 3c, 4a, and 4b each have 2 electrodes, sensors having more than 2 electrodes may also be easily made using method 200.

Figure 5:
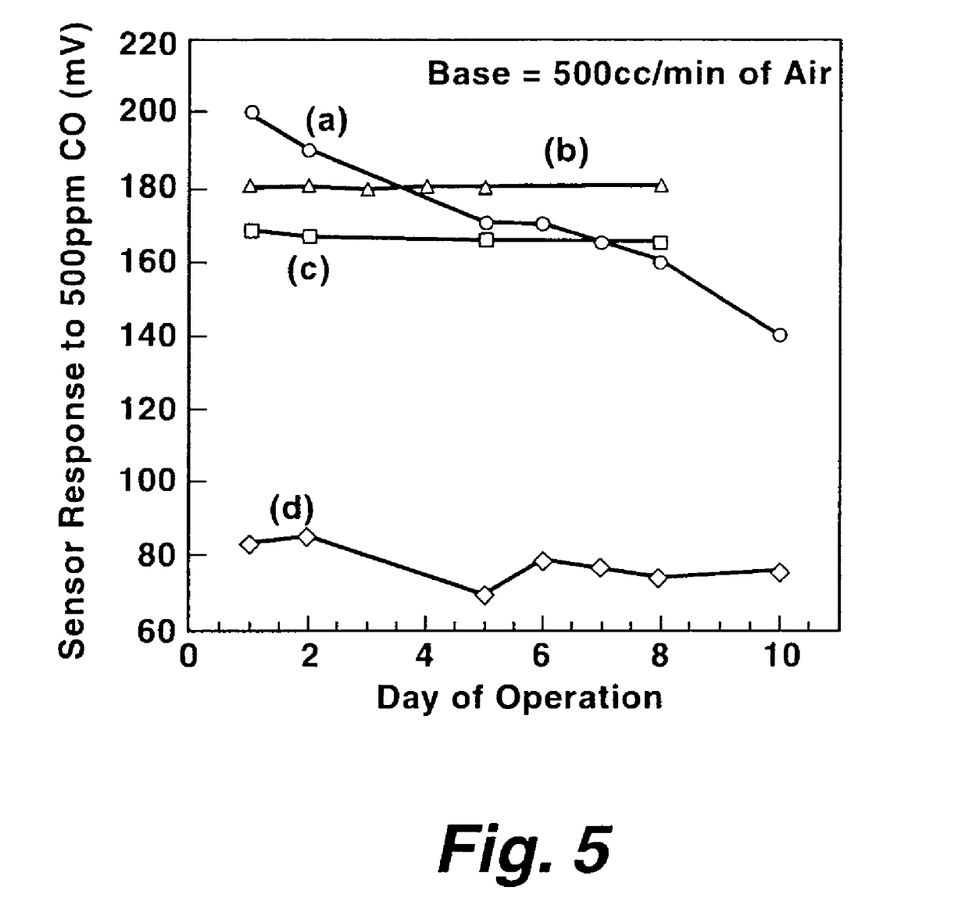
FIG. 5 is a plot of response to 500 ppm CO for: (a) a prior art Pt/YSZ/Au bulk sensor at 400° C.; (b) a Pt/YSZ/Au tape-cast sensor at 500° C.; (c) a Pt/YSZ/Au tape-cast sensor at 500° C.; and (d) a bulk Pt/$Ce_{0.8}Gd_{0.2}O_{1.9}$/Au sensor at 400° C.

The response of sensor 100 is very stable over time, as illustrated by the response of Pt/YSZ/Au tape-cast sensors, manufactured according by the method described herein, to CO. FIG. 5 is a plot of response to 500 ppm CO for: (a) a prior art Pt/YSZ/Au bulk sensor at 400° C.; (b) a Pt/YSZ/Au tape-cast sensor at 500° C.; (c) a Pt/YSZ/Au tape-cast sensor at 500° C.; and (d) a bulk Pt/$Ce_{0.8}Gd_{0.2}O_{1.9}$ (also referred to herein as "CGO")/Au sensor at 400° C. over a period ranging from about 8 to 10 days. As seen in FIG. 5, the response of the bulk Pt/YSZ/Au sensor ((a) in FIG. 5) decays by over 30% in 10 days, whereas that of the tape-cast Pt/YSZ/Au sensors ((b) and (c) in FIG. 5) each fluctuate less than 2% over an eight day period. The response stability of the tape-cast sensors is also better than that observed for the bulk Pt/CGO/Au sensor ((d) in FIG. 5).

Figure 6:
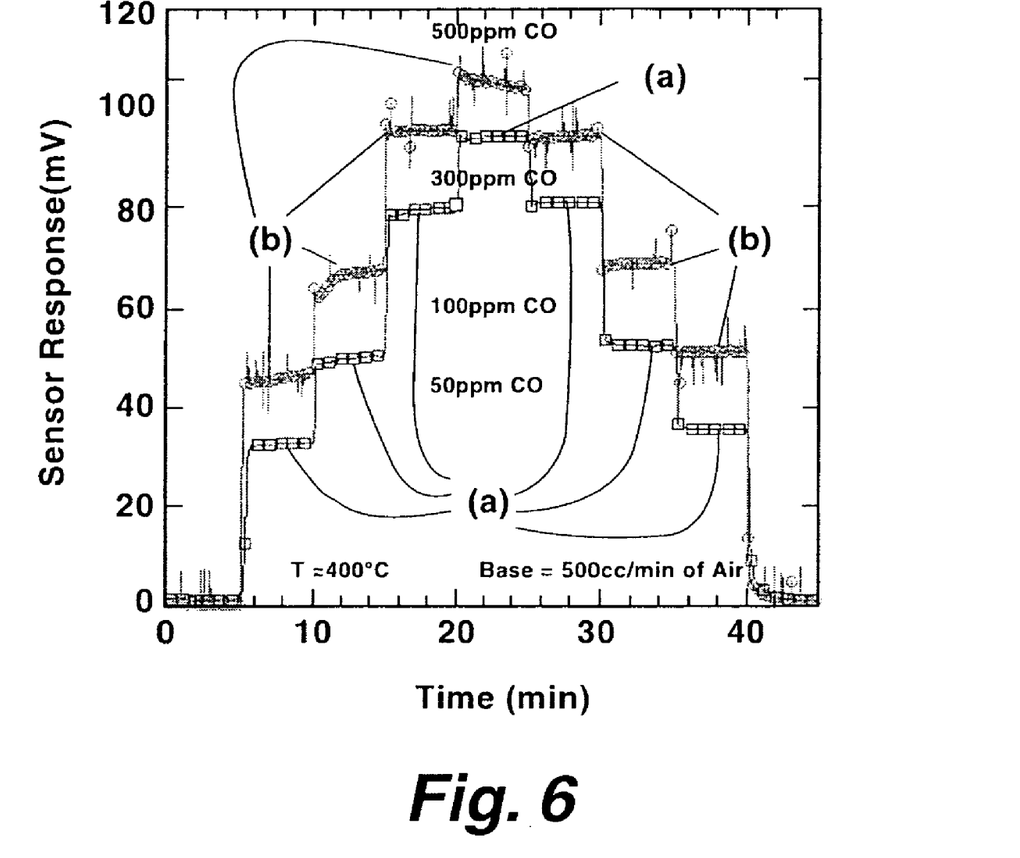
FIG. 6 is a plot of response for: (a) bulk and (b) tape-cast Pt/CGO/Au sensors as a function of time for different CO concentrations.

Sensor 100 also exhibits improved sensitivity over bulk sensors of similar composition. FIG. 6 is a plot of response for: (a) bulk and (b) tape-cast Pt/CGO/Au sensors as a function of time for different CO concentrations. As seen in FIG. 6, the tape-cast sensor (b) is more sensitive than the bulk sensor (a) over the entire range of CO concentrations studied.

Figure 7:
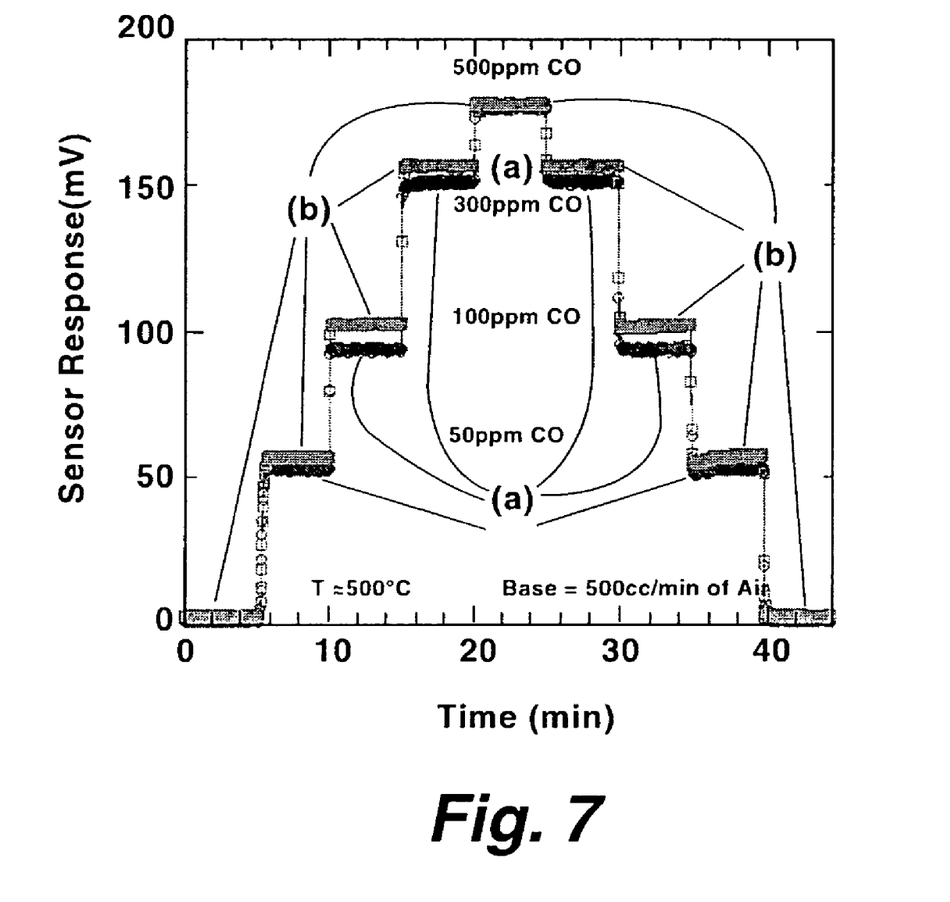
FIG. 7 is a plot of response for two identical Pt/YSZ/Au sensors that sere made using the tape-casting process described herein.

The difference in the response observed in FIG. 5 for the two tape-cast sensors can be attributed to the fact that the sensors did not have the same dimensions and were made from two different batches of tape-cast electrolyte. As shown in FIG. 7, two identical Pt/YSZ/Au sensors, made using the tape-casting process described herein, exhibited a CO response within 10% of each other, thus demonstrating the stability and reproducibility of sensors made by the tape-casting methods described herein.

Sensor 100 may be operated in any one of a zero current mode, a zero voltage bias mode, a positive current bias mode, or a positive voltage bias mode. In the zero current mode, the sensor behaves like a true mixed-potential sensor, where a voltage develops depending on the rates of the various electrochemical reactions occurring at the different electrodes. This voltage is more negative than the equilibrium voltage for reducing gases like hydrocarbons (HCs), CO and NO, and is more positive than the equilibrium voltage for oxidizing gases such as $NO_2$. When compared to the Pt electrode, the voltage developed in the zero current mode is greater in magnitude on the La-chromite or Au electrodes. Therefore, when operated in the zero-current mode with the Pt electrode connected to the instrument positive and Au or La-chromite electrode connected to instrument negative, HCs, NO, and CO each produce a positive voltage response, whereas $NO_2$ produces a negative voltage response. When operated in the zero-voltage mode, the same sensor would yield a negative current for HCs, NO, and CO and a positive current for $NO_2$.

In either a voltage bias mode or a current bias mode, the sensor response is a mixed potential response superimposed on a resistance change. This resistance change is due to the electrode reactions in which resistance decreases with the addition of NO, $NO_2$, or non-methane hydrocarbons. When the sensor is operated in a positive current bias mode, the resistance change results in a lowering of the sensor voltage when NO and $NO_2$ are introduced. The magnitude of this response with respect to NO and $NO_2$ is very similar. These two gases tend to give identical sensor responses in the bias mode, especially when their response in the zero-bias mode is negligible. On the other hand, the bias current can be adjusted so as to zero out the voltage generated due to the hydrocarbons. Similarly, in the positive voltage-bias mode, the response to NO and $NO_2$ is an increase in current, while the HC interference can be cancelled out. Thus, Pt/YSZ/La-chromite sensors act as HC sensor in the zero-bias mode and as total NOx sensors in the positive bias mode.

Figure 8:
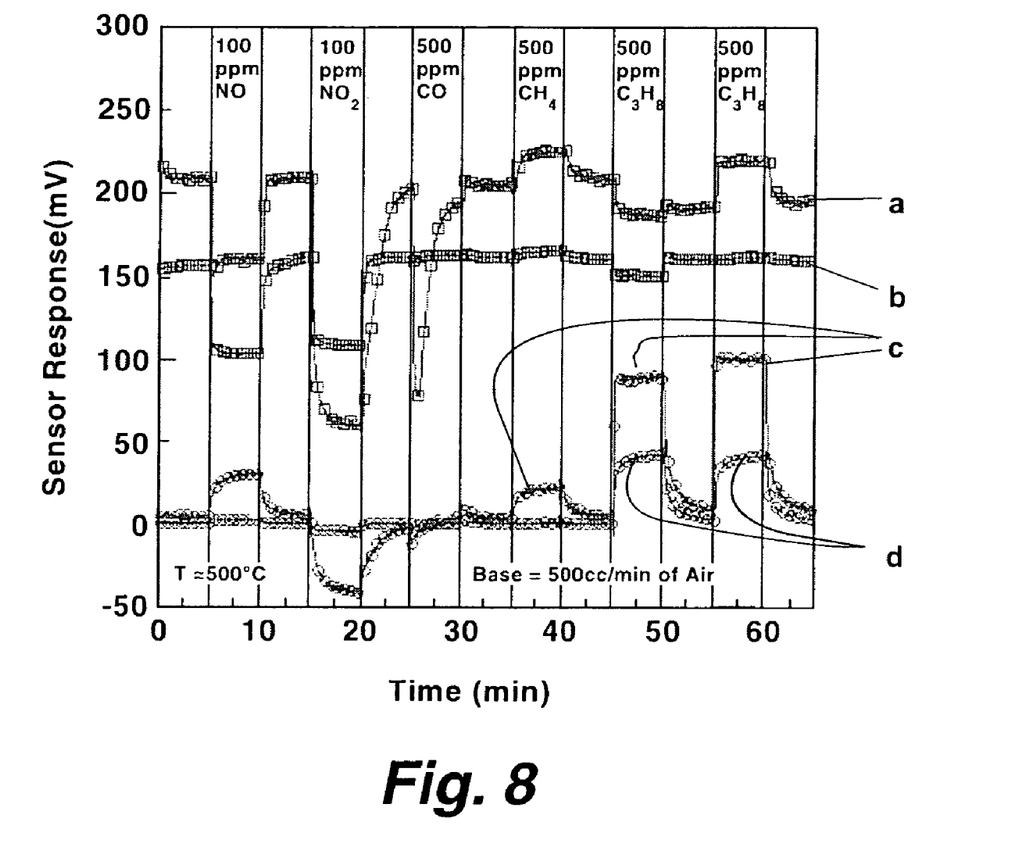
FIG. 8 is a plot of Pt/YSZ/$La_{0.8}Sr_{0.2}CrO_3$ sensors: a) bulk sensor at positive current (0.5 µA) bias; b) tape-cast sensor at positive current (0.5 µA) bias; c) bulk sensor at zero current (0.0 µA) bias; and d) tape-cast sensor at zero current (0.0 µA) bias.

FIG. 8 is a plot of the response of the following Pt/YSZ/$La_{0.8}Sr_{0.2}CrO_3$ sensors: a) bulk sensor at positive current (0.5 µA) bias; b) tape-cast sensor at positive current (0.5 µA) bias; c) bulk sensor at zero current (0.0 µA) bias; and d) tape-cast sensor at zero current (0.0 µA) bias. The sensors studied in FIG. 8 were prepared by either the tape-cast process described herein or the prior art bulk process. At zero current bias, both the tape-cast sensor (d) and bulk sensor (c) respond to both NOx and to non-methane hydrocarbons (here, propylene and propane). Although the sensitivity of the tape-cast sensor (b) in this instance is lower than that of the bulk sensor (b), the tape-cast sensor has greater hydrocarbon selectivity. When the sensors are operated in the positive bias mode, NO and $NO_2$ produce identical responses in the tape-cast sensor (b in FIG. 8), whereas these species produce different responses in bulk sensors.

In currently available bulk sensors, NO and $NO_2$ responses depend upon environmental conditions, making any determination of total concentration of NOx gases from the sensor output difficult. In many cases, either additional measurements are necessary or catalysts or pumping cells are required to convert all the NOx gases to a single specie. Because NO and $NO_2$ produce identical responses in the tape-cast sensor, sensor 100 is particularly suitable for use as a total NOx sensor without using any additional gas or requiring additional data processing or measurements.

The ability of sensor 100 to operate in various bias modes enables sensor 100 to detect other gaseous species without interference due to the presence of other gases. When operated under a bias mode, for example, tape-cast sensor 100 can be used as an ammonia sensor with no interference from CO or hydrocarbons.

Sensor 100 is capable of detecting a variety of gaseous species including, but not limited to, carbon monoxide, hydrocarbons, ammonia, nitrogen oxides, sulfur oxides, alcohols, either individually or in combination with each other.

While typical embodiments have been set forth for the purpose of illustration, the foregoing description should not be deemed to be a limitation on the scope of the invention. Accordingly, various modifications, adaptations, and alternatives may occur to one skilled in the art without departing from the spirit and scope of the present invention.

The invention claimed is:

1. A method of making a solid state electrochemical sensor, the sensor comprising a plurality of electrodes partially disposed within an electrolyte, the method comprising the steps of:
   a) providing the electrolyte;
   b) casting the electrolyte to form an electrolyte tape, wherein the electrolyte tape has a wet first surface;
   c) providing the plurality of electrodes;
   d) contacting a portion of each of the plurality of electrodes with a first portion of the wet first surface;
   e) contacting a second portion of the wet first surface with the portion of each of the plurality of electrodes and the first portion of the wet first surface, wherein each of the plurality of electrodes is partially embedded within the electrolyte;
   f) drying the electrolyte tape and the partially embedded plurality of electrodes to form a green sensor body; and
   g) sintering the green sensor body to form the solid state electrochemical sensor.

2. The method according to claim 1, wherein the electrochemical sensor is a non-Nernstian sensor.

3. The method according to claim 2, wherein the non-Nerustian sensor is a mixed potential sensor.

4. The method according to claim 1, wherein the step of casting the electrolyte to form an electrolyte tape comprises the steps of:
   a) combining the electrolyte with a solvent, a binder, and a plasticizer to form a slurry;
   b) milling the slurry; and
   c) casting the slurry onto a carrier.

5. The method according to claim 1, wherein the electrolyte comprises an ionic conducting material.

6. The method according to claim 3, wherein the ionic conducting material is an oxide having one of a fluorite crystal structure, a perovskite crystal structure, a brown-millerite crystal structure, a pyrochlore crystal structure, and a beta-alumina crystal structure.

7. The method according to claim 5, wherein the electrolyte is one of yttria stabilized zirconia, gadolinia stabilized ceria, and combinations thereof.

8. The method according to claim 1, wherein the plurality of electrodes comprises at least one electronically conducting material.

9. The method according to claim 8, wherein the at least one electronically conducting material comprises at least one of an oxide, a metal, a semiconductor, and combinations thereof, and wherein the at least one electronically conducting material has an electronic conductivity of greater than 10 mS/cm at a temperature in a range from about 300° C. to about 1000° C.

10. The method according to claim 1, wherein the plurality of electrodes comprises at least one of platinum, gold, a lanthanide based oxide, a zirconium based oxide, and combinations thereof.

11. The method according to claim 10, wherein the lanthanide based oxide is one of a lanthanum chromium based oxide, a lanthanum cobalt based oxide, a lanthanum manganese based oxide, and combinations thereof.

12. The method according to claim 10, wherein the zirconium based oxide is a terbium doped zirconium based oxide.

13. The method according to claim 1, wherein the plurality of electrodes comprises at least one of a metal wire, a metal foil, a ceramic pellet, and a ceramic tape.

14. The method according to claim 1, further including the step of cutting the green sensor body to form a plurality of green sensor bodies.

15. The method according to claim 1, wherein the sensor is operable in one of a zero current bias mode, a zero voltage bias mode, a positive current bias mode, and a positive voltage bias mode.

16. The method according to claim 1, wherein the sensor detects one of carbon monoxide, hydrocarbons, ammonia, nitrogen oxides, sulfur oxides, alcohols, and combinations thereof.

17. A method of making a green sensor body, the method comprising the steps of:
   a) providing the electrolyte;
   b) casting the electrolyte to form an electrolyte tape, wherein the electrolyte tape has a wet first surface in contact with a carrier and a second surface opposite the wet first surface, the second surface being exposed to air;
   c) partially drying the second surface for a predetermined time;
   d) reversing the electrolyte tape such that the wet first surface is exposed to air and the partially dried second surface contacts the carrier;
   e) providing at least a first electrode and a second electrode;
   f) contacting a portion of each of the first electrode and the second electrode with a first portion of the wet first surface;
   g) contacting a second portion of the wet first surface with the portion of each of the first electrode and the second electrode and the first portion of the wet first surface, wherein the first and second electrodes are partially embedded within the electrolyte; and
   h) drying the electrolyte tape and the partially embedded first electrode and second electrode to form a green sensor body.

18. A method of making a solid state mixed potential sensor, the sensor comprising at least a first electrode and a second electrode partially disposed within an electrolyte, the method comprising the steps of:
   a) providing the electrolyte;
   b) casting the electrolyte into an electrolyte tape, wherein the electrolyte tape has a wet first surface in contact with a carrier and a second surface opposite the wet first surface, the second surface being exposed to air;
   c) partially drying the second surface for a predetermined time;
   d) reversing the electrolyte tape such that the wet first surface is exposed to air and the partially dried second surface contacts the carrier, wherein the first surface is wet;
   e) providing at least a first electrode and a second electrode;
   f) contacting a portion of the first electrode and the second electrode with a first portion of the wet first surface;
   g) contacting a second portion of the wet first surface with the portion of the first electrode and the second electrode and the first portion of the wet first surface, wherein the first and second electrodes are partially embedded within the electrolyte tape;
   h) drying the electrolyte tape and the partially embedded first and second electrodes to form a green sensor body; and
   i) sintering the green sensor body to form the solid state mixed potential sensor.

* * * * *